United States Patent [19]

Brenner et al.

[11] Patent Number: 5,356,887
[45] Date of Patent: Oct. 18, 1994

[54] PHARMACEUTICAL COMPOSITIONS CONTAINING INSOLUBLE CALCIUM SALTS OF AMINO-HYDROXYBUTYLIDENE BISPHOSHONIC ACIDS

[75] Inventors: Gerald S. Brenner, Norristown; Drazen Ostovich, Hatfield, both of Pa.

[73] Assignee: Merck & Co., Inc., Rahway, N.J.

[21] Appl. No.: 118,832

[22] Filed: Sep. 7, 1993

Related U.S. Application Data

[63] Continuation of Ser. No. 924,432, Jul. 31, 1992, abandoned, which is a continuation of Ser. No. 714,467, Jun. 13, 1991, abandoned, which is a continuation of Ser. No. 561,026, Aug. 1, 1990, abandoned, which is a continuation-in-part of Ser. No. 472,987, Jan. 31, 1990, abandoned.

[51] Int. Cl.$^5$ .............................. A61K 31/66
[52] U.S. Cl. ..................................... 514/108
[58] Field of Search ................... 514/107, 108

[56] References Cited

U.S. PATENT DOCUMENTS

| | | | |
|---|---|---|---|
| 3,962,432 | 6/1976 | Schmidt-Dünker | 514/108 |
| 3,962,433 | 6/1976 | Worms et al. | 514/121 |
| 4,134,969 | 1/1979 | Schmidt-Dünker | 424/49 |
| 4,446,052 | 5/1984 | Sunberg et al. | 252/315.1 |
| 4,578,376 | 3/1986 | Rosini | 514/108 |
| 4,621,077 | 11/1986 | Rosini et al. | 514/108 |
| 4,624,947 | 11/1986 | Blum et al. | 514/108 |
| 4,761,406 | 8/1988 | Flora et al. | 514/86 |
| 4,922,007 | 5/1990 | Kieczykowski et al. | 562/13 |
| 4,942,157 | 7/1990 | Gall et al. | 514/108 |

*Primary Examiner*—Marianne M. Cintins
*Assistant Examiner*—T. J. Criares
*Attorney, Agent, or Firm*—Joanne M. Giesser; Melvin Winokur; Paul D. Matukaitis

[57] ABSTRACT

Crystalline and amorphous insoluble calcium salts of bisphosphonic acids may be formulated to provide compositions suitable for I.M. (intramuscular) and S.C. (subcutaneous) administration. As compared to solutions of the soluble salts of bisphosphonic acids, suspensions of the crystalline and amorphous calcium salts provide slow systemic release of the bisphosphonic acid and reduce tissue damage and localized pain and irritation when used in the treatment of disturbances involving calcium or phosphate metabolism, in particular, the treatment and prevention of diseases involving bone resorption, especially osteoporosis, Paget's disease, malignant hypercalcemia, and metastatic bone disease.

20 Claims, No Drawings

PHARMACEUTICAL COMPOSITIONS CONTAINING INSOLUBLE CALCIUM SALTS OF AMINO-HYDROXYBUTYLIDENE BISPHOSHONIC ACIDS

This application is a continuation of Ser. No. 07/924,432, filed Jul. 31, 1992, now abandoned, which is a continuation of Ser. No. 07/714,467, filed on Jun. 13, 1991, now abandoned, which is a continuation of Ser. No. 07/561,026, filed Aug. 1, 1990, now abandoned which is a continuation-in-part of copending application Ser. No. 472,987, filed Jan. 31, 1990, now abandoned.

The present invention relates to suspensions of crystalline and amorphous insoluble calcium salts of bisphosphonic acids, processes for their preparation, pharmaceutical compositions containing them, and methods for their use in the treatment and prevention of diseases involving bone resorption, especially osteoporosis, Paget's disease, malignant hypercalcemia, and metastatic hone disease.

BACKGROUND OF THE INVENTION

Certain bisphosphonic acids, for example methylene bisphosphonic acid, dichloromethylene bisphosphonic acid, (1-hydroxyethylidene)bisphosphonic acid, (2-aminoethylidene)bisphosphonic acid, (3-amino-1-hydroxypropylidene)bisphosphonic acid and (4-amino-1-hydroxybutylidene)bisphosphonic acid have utility in the treatment of diseases characterized by abnormal calcium metabolism, in particular, diseases involving bone resorption, especially osteoporosis, Paget's disease, malignant hypercalcemia, and metastatic bone disease.

There is a long-felt need to improve the pharmacological properties of bisphosphonic acids. An important disadvantage of bisphosphonic acids in pharmaceutical applications is that they can cause tissue damage, localized pain and irritation following intramuscular or subcutaneous injection. Another disadvantage is that the level of bisphosphonic acid in the blood after intravenous injection reaches a peak within a couple of hours and levels off to less than 10% of the peak value within 5 hours after intravenous injection. As a result, many bisphosphonic acids are taken up in significant quantity by the liver or excreted by the kidneys. When administered orally, bisphosphonic acids suffer from the problem of low bioavailability and, in addition, may exhibit gastrointestinal side effects, particularly with the large oral doses required to provide therapeutic efficacy. The pharmacological profile of bisphosphonic acids is therefore not as favorable as one might desire.

U.S. Pat. No. 4,621,077, issued Nov. 4, 1986, to Rosini and Staibano discloses pharmaceutical compositions comprising (4-amino-1-hydroxybutylidene)-1,1-bisphosphonic acid (ABP) or a water-soluble (sodium, aniline or lysine) salt thereof. The insoluble, calcium salts of ABP are not disclosed.

U.S. Pat. No. 4,446,052, issued May 1, 1984, to Sunberg and Benedict discloses a gel comprising di[(3-amino-1-hydroxypropylidene)-1,1-bisphosphonic acid] tricalcium salt in water. The gel is disclosed to be useful for the treatment of certain disorders of calcium metabolism in warm blooded animals. No suggestion is made that the pharmaceutical compositions containing insoluble salts can be modified to avoid undesirable properties, such as gel formation, caking, particle size growth, relatively high viscosity or poor syringability. It is important to note that a gel formulation suffers severe difficulties in S.C. or I.M. administration and is to be avoided. The suspensions of the present invention overcome such problems inherent with gel formulations.

Three insoluble calcium salts of (4-amino-1-hydroxybutylidene)-1,1-bisphosphonic acid (ABP) wherein the molar ratio of ABP to calcium is 1:1, 2:1, or approximately 3:4 (hereinafter referred to as (ABP)Ca, (ABP)$_2$Ca, and (ABP)$_3$Ca$_4$, respectively) as suspensions in an aqueous pharmaceutical composition at a pH from about 6 to about 7.5 each have pharmaceutical properties very similar to the soluble sodium salts of ABP, but with a much lower propensity to cause tissue damage, pain and irritation following intramuscular or subcutaneous injection. Moreover, the pharmaceutical compositions of the present invention comprising (ABP)Ca, (ABP)$_2$Ca, or (ABP)$_3$Ca$_4$ have very good physical stability (as indicated by lack of caking or gelling of the suspension). The systemic release of ABP from the calcium salts is slow which results in a lower uptake of ABP by the liver as compared to the sodium salts. This slow systemic release results in the desired concentration of ABP in solution and provides benefits in a number of therapeutic uses of ABP including the treatment and prevention of diseases involving bone resorption, especially osteoporosis, Paget's disease, malignant hypercalcemia, and metastatic bone disease.

It is therefore a purpose of this invention to provide an aqueous suspension of insoluble calcium salts of ABP. It is a further purpose of this invention to provide a pharmaceutical compositions comprising an aqueous suspension of an insoluble calcium salt of ABP wherein the molar ratio of ABP to calcium is 1:1, 2:1, or approximately 3:4. It is a further purpose of this invention to provide methods of treatment of calcium disorders virtually without side effects of tissue damage, pain and irritation following intramuscular or subcutaneous injection. Finally, this invention provides methods for the treatment of calcium disorders which require a slow systemic release of ABP.

DESCRIPTION OF THE INVENTION

The present invention relates to aqueous suspensions comprising from about 0.05% to about 3% [(4-amino-1-hydroxybutylidene)-1,1-bisphosphonic acid] monocalcium salt, (ABP)Ca, di[(4-amino-1-hydroxybutylidene)-1,1-bisphosphonic acid] monocalcium salt, (ABP)$_2$Ca or tri[(4-amino-1-hydroxybutylidene)-1,1-bisphosphonic acid] tetracalcium salt, (ABP)$_3$Ca$_4$. Relative to the soluble sodium salts of ABP these suspensions of the insoluble calcium salts of ABP provide slow systemic release of ABP and significantly reduced tissue damage, pain and irritation upon intramuscular or subcutaneous administration.

In its narrower aspects this invention is directed to the pharmaceutical compositions comprising (ABP)Ca, (ABP)$_2$Ca, or (ABP)$_3$Ca$_4$ and to improved methods of treating disorders which can normally beneficially be treated with a bisphosphonic acid, which method comprises the step of systemically administering the insoluble (ABP)Ca, (ABP)$_2$Ca, or (ABP)$_3$Ca$_4$ salt to an afflicted human or warm-blooded animal.

By "[(4-amino-1-hydroxybutylidene)-1,1-bisphosphonic acid] monocalcium salt" herein is meant the calcium salt of (4-amino-1-hydroxybutylidene)-1,1-bisphosphonic acid which has a molar ratio of bisphosphonic acid:calcium of 1:1 and may optionally be present as the monohydrate. By "di[(4-amino-1-hydroxybutylidene)-1,1-bisphosphonic acid] monocalcium salt" herein is meant the calcium salt of (4-amino-1-hydroxybutylidene)-1,1-bisphosphonic acid which has a molar ratio of bisphosphonic acid:calcium of 2:1. By "tri[(4-amino-1-hydroxybutylidene)-1,1-bisphosphonic acid] tetracalcium salt" herein is meant the calcium salt of (4-amino-1-hydroxybutylidene)-1,1-bisphosphonic acid which has a molar ratio of bisphosphonic acid:calcium which may range from 4:5 to 2:3, but is preferably, approximately 3:4.

By "insoluble" herein is meant to mean that the concentration of the compound ABP (as the free acid) in the supernatant phase is 1.0 mg/ml or less.

Relative to the soluble salts of ABP (such as (ABP)Na, (4-amino-1-hydroxybutylidene)-1,1-bisphosphonic acid monosodium salt) and to ABP itself, these suspensions of the insoluble calcium salts of ABP ((ABP)Ca, (ABP)$_2$Ca or (ABP)$_3$Ca$_4$) cause less tissue damage, pain and irritation when administered intramuscularly or subcutaneously to humans and other warm-blooded animals. In particular, the (ABP)Ca salt, being intrinsically neutral in pH, remains relatively non-irritating following intramuscular or subcutaneous administration and subsequent diffusion of the pharmaceutical vehicle. Additionally, the insoluble (ABP)Ca, (ABP)$_2$Ca, or (ABP)$_3$Ca$_4$ salts are characterized by a slow systemic release as compared to the soluble salts of ABP and to ABP, itself. Nevertheless, the insoluble (ABP)Ca, (ABP)$_2$Ca, or (ABP)$_3$Ca$_4$ salts have similar biological properties to the soluble salts of ABP or ABP, itself. These properties make the insoluble (ABP)Ca, (ABP)$_2$Ca, and (ABP)$_3$Ca$_4$ salts extremely useful in a number of pharmaceutical applications of bisphosphonic acids of the prior art.

The pharmaceutical compositions of the suspensions of the insoluble calcium salts of the present invention when administered by intramuscular or subcutaneous injection avoid the inconvenience of intravenous administration while maintaining the advantages of parenteral administration i.e. good bioavailability.

The intrinsically neutral crystalline insoluble calcium salt of ABP, (ABP)Ca, is obtained by the mixing of a solution of a soluble salt of (4-amino-1-hydroxybutylidene)-1,1-bisphosphonic acid or the free acid of ABP at a pH above 6 with a solution of a soluble salt of calcium. A suitable example of such soluble salts of ABP is monosodium ABP and a suitable example of such soluble salts of calcium is CaCl$_2$. Preferably, the amounts are stoichiometric, (i.e., a ABP:Ca ratio of 1:1). Prior to mixing the pH of the solution of the soluble ABP salt or ABP free acid is adjusted to about 9 by the addition of a strong inorganic or organic base (such as NaOH) and the solution is heated (at 50–100° C.) to facilitate the reaction. A short time after the mixing of the solution of the soluble salt of ABP and the soluble calcium salt, crystallization commences. After cooling to room temperature and the completion of crystallization, the crystalline (ABP)Ca is collected by filtration. The crystalline (ABP)Ca is then micronized (or otherwise reduced in particle size), suspended in a suitable isotonic vehicle containing an appropriate suspending agent (such as that composed of sodium carboxymethylcellulose and sodium chloride in water) and sterilized prior to administration.

The crystalline insoluble calcium salt of ABP, (ABP)$_2$Ca, is obtained by the mixing of a solution of a soluble salt of (4-amino-1-hydroxybutylidene)-1,1-bisphosphonic acid or the free acid of ABP at a pH of about 1.5 to about 2.5 with a solution of a soluble salt of calcium. A suitable example of such soluble salts of ABP is monosodium ABP and a suitable example of such soluble salts of calcium is CaCl$_2$. Preferably, the amounts are stoichiometric, (i.e., a ABP:Ca ratio of 2:1). Prior to mixing the pH of the solution of the soluble ABP salt or ABP free acid is adjusted to from about 1.5 to about 2.5 by the addition of a strong inorganic or organic acid (such as HCl) and the solution is heated (at 50–90° C.) to facilitate the reaction. A short time after the mixing of the solution of the soluble salt of ABP and the soluble calcium salt, crystallization commences. After cooling to room temperature and the completion of crystallization, the crystalline (ABP)$_2$Ca is collected by filtration. The crystalline (ABP)$_2$Ca is then micronized (or otherwise reduced in particle size), sterilized and suspended in a suitable isotonic vehicle containing an appropriate suspending agent and buffering agent (such as that composed of sodium carboxymethylcellulose, sodium chloride and sodium acetate in water) prior to administration.

A solution of the amorphous insoluble calcium salt of ABP, (ABP)$_3$Ca$_4$, is obtained by mixing of a solution of a soluble salt of (4-amino-1-hydroxybutylidene)-1,1-bisphosphonic acid or the free acid of ABP at a pH of about 9 to about 13 with a solution of a soluble salt of calcium. A suitable example of such soluble salts of ABP is monosodium ABP and a suitable example of such soluble salts of calcium is CaCl$_2$. Preferably, the amounts are stoichiometric, (i.e., a ABP:Ca ratio of approximately 3:4). Prior to mixing, the pH of the solution of the soluble ABP salt is adjusted to from about 9 to about 13 by the addition of a strong inorganic or organic base (such as NaOH) and the solution is buffered by the addition of a suitable buffering agent (such as 2-amino-2-hydroxymethyl-1,3-propanediol, Tris). Upon mixing the solution of the soluble salt of ABP and the soluble calcium salt, precipitation commences. Following dilution to a known volume and sterilization, the suspension of the amorphous salt (ABP)$_3$Ca$_4$ may be administered.

As hereinbefore indicated, the suspensions of the insoluble (ABP)Ca, (ABP)$_2$Ca, and (ABP)$_3$Ca$_4$ salts of the present invention (in particular, the (ABP)Ca salt) have a dramatically lower propensity of causing pain, irritation and damage to soft tissues upon intramuscular or subcutaneous administration than the bisphosphonic acids of the prior art.

The suspensions of the insoluble (ABP)Ca, (ABP)$_2$Ca, and (ABP)$_3$Ca$_4$ salts of this invention have also been found to provide slow systemic release of ABP. This significantly alleviates the problem of liver and renal toxicity of ABP itself. For example, shortly after intravenous dosing of sodium ABP solution, there is a high level of the drug in the bloodstream. The body responds by accumulating the drug in the liver and by excreting an important amount of the drug through the kidneys. However, upon subcutaneous administration of a pharmaceutical formulation of either the (ABP)Ca salt, the (ABP)$_2$Ca salt, or the (ABP)$_3$Ca$_4$ salt, the insoluble salt remains at the injection site and is only slowly released into the bloodstream. Therefore, the level of the drug in the bloodstream is never very high and consequently, the uptake by the liver and excretion by the kidneys is lower than in the case of the soluble sodium ASP solution.

Depending on the condition to be treated a pharmaceutical formulation containing the suspension of (ABP- )Ca salt, the (ABP)$_2$Ca salt, or the (ABP)$_3$Ca$_4$ salt is administered by either intramuscular or subcutaneous injection. Examples of conditions which may be treated by administration of a safe and effective amount of the (ASP)Ca salt, the (ABP)$_2$Ca salt, or the (ABP)$_3$Ca$_4$ salt include disturbances involving calcium or phosphate metabolism, in particular, the treatment and prevention of diseases involving bone resorption, especially osteoporosis, Paget's disease, malignant hypercalcemia, and metastatic bone disease.

In addition to utility in the treatment and prevention of diseases involving bone resorption (especially osteoporosis, Paget's disease, malignant hypercalcemia, and metastatic bone disease), suspensions containing the (ABP)Ca salt, the (ABP)$_2$Ca salt, or the (ABP)$_3$Ca$_4$ salt have utility in other applications that require slow release of bisphosphonic acids such as the treatment of periodontal disease, the minimization of alveolar bone loss in tooth sockets following extraction, the prevention of skin and soft tissue calcification, and other treatments in which systemic or localized application of a bisphosphonic acid is desired.

The (ABP)Ca salt, the (ABP)$_2$Ca salt, and the (ABP)$_3$Ca$_4$ salt are administered as an injectable suspension comprising the (ABP)Ca salt, the (ABP)$_2$Ca salt, or the (ABP)$_3$Ca$_4$ salt and a suitable pharmaceutical carrier. These injectable suspensions may be formulated according to known art, using suitable non-toxic, parenterally-acceptable diluents or solvents, such as 1,2-propanediol, water, Ringer's solution, dextrose solution or isotonic sodium chloride solution. These injectable suspensions may further contain excipients suitable for the manufacture of aqueous suspensions. Such excipients may be:

(1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be
 (a) a naturally-occurring phosphatide such as lecithin,
 (b) a condensation product of an alkylene oxide with a fatty acid, for example, polyoxyethylene stearate,
 (c) a condensation product of an ethylene oxide with a long chain aliphatic alcohol, for example, heptadecaethyleneoxycetanol,
 (d) a condensation product of ethylene oxide with a partial ester derived from a fatty acid and a hexitol such as polyoxyethylene sorbital monooleate, or
 (e) a condensation product of ethylene oxide with a partial ester derived from a fatty acid and a hexitol anhydride, for example polyoxyethylene sorbitan monooleate.

Such suspensions may further contain microcrystalline cellulose for imparting bulk and methylcellulose as a viscosity enhancer.

The aqueous suspensions may also contain one or more preservatives, for example, ethyl or n-propyl p-hydroxybenzoate, and antioxidants and the like may be incorporated as required.

In addition, the aqueous suspension may be buffered if necessary to an physiologically appropriate pH by the addition of a suitable buffer, such as sodium acetate, sodium lactate, sodium benzoate or Tris.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients may also be present.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. These compositions may be prepared by the addition of an antioxidant such as ascorbic acid.

To minimize irritation upon administration, it is preferred that the mixture of the aqueous suspension of (ABP)$_2$Ca, or (ABP)$_3$Ca$_4$ and the pharmaceutical carrier be buffered to a pH of 5.5–7.5 by the addition of an appropriate buffering agent (such as sodium acetate, sodium lactate, sodium benzoate or Tris). Being intrinsically neutral in pH, the (ABP)Ca salt may not require the addition of a buffering agent when in an aqueous suspension with a pharmaceutical carrier. A pharmaceutical composition in unit dosage form contains from about 0.01 mg/ml to about 300 mg/ml, (ABP)Ca, (ABP)$_2$Ca, or (ABP)$_3$Ca$_4$, preferably from about 0.1 mg/ml to about 30 mg/ml.

Due to the slow systemic release, a pharmaceutical formulation containing a suspension of the (ABP)Ca salt, the (ABP)$_2$Ca salt or the (ABP)$_3$Ca$_4$ salt is effective at very low dosage rates. Due to the low tissue damaging propensity, rather high dosages can be used without serious adverse side effects. Daily dosage rates are from about 0.001 mg/kg to about 10 mg/kg, preferably from about 0.01 mg/kg to about 1.0 mg/kg. Dosages are expressed as mg ABP per kg body weight of the patient.

A pharmaceutical formulation containing the (ABP)Ca salt, the (ABP)$_2$Ca salt, or the (ABP)$_3$Ca$_4$ salt may also be administered on an intermittent basis. For the treatment or prophylaxis of diseases involving bone resorption a typical daily primary I.M. or S.C. dose which lies within the range of from about 0.001 mg/kg to about 10 mg/kg may be administered over a period of about 1 day to about 90 days and then, if necessary a sustaining dose approximately equal to the primary dose may be administered at weekly, semiweekly, semimonthly, monthly, bimonthly, quarterly, semiannual, annual or biannual intervals. Dosages are expressed as mg ABP per kg body weight of the patient.

The following examples are given for the purpose of illustrating the present invention and shall not be construed as being limitations on the scope or spirit of the instant invention.

EXAMPLE 1

Preparation of
(4-Amino-1-hydroxybutylidene)-1,1-bisphosphonic acid monosodium salt trihydrate Ten grams (37.4 mmol) of (4-amino-1-hydroxybutylidene)-1,1-biphosphonic acid, (ABP) was suspended in 300 mL of distilled deionized water with vigorous stirring at 25° C. The pH was 2.27 and was titrated to pH 4.3 to 4.4 by the gradual addition of 7.5 ml (37.4 mmol) 5N sodium hydroxide solution, resulting in a clear solution.

The clear solution was filtered through a medium sintered-glass funnel to remove any insoluble material. Twenty percent of the filtrate (~60 mL) was added over 5 minutes to 400 mL of 95% ethanol at 20°–25° C. with vigorous stirring and aged for one hour.

The remaining 240 mL of aqueous solution was added over 15 minutes and the mixture aged for 2 hours at 20°–25° C. The white sodium salt was collected by filtration, washed with 100 ml of 2:1 EtOH:H$_2$O and air dried at 40° C. to yield 11.25 g (93%) of (4-amino-1-hydroxybutylidene)-1,1-bisphosphonic acid monosodium salt trihydrate.

The title compound may also be prepared as described in U.S. Pat. No. 4,922,007, issued May 1, 1990 to Kieczykowski et al.

EXAMPLE 2

Preparation of Crystalline (ABP)Ca Salt Monohydrate

[(4-Amino-1-hydroxybutylidene)-1,1-bisphosphonic acid] monosodium salt trihydrate (3.25 g, 0.01 mmol) was suspended in 50 ml of water. To this solution was added 10 ml of 1.0M aqueous NaOH. Upon addition of NaOH, complete dissolution occurs. To this solution was added 10 ml of 1.0M aqueous CaCl$_2$ solution with stirring. Upon addition of CaCl$_2$, heavy precipitation of amorphous (ABP)Ca salt was observed. Heating of the slurry at approx. 90° C. for approx. 2 hours resulted in complete crystallization to product. The crystalline product was isolated by filtration, washed with water and air dried to yield 2.74 g (89.8% yield) crystalline (ABP)Ca as the monohydrate.

Anal. Calcd. for C$_4$H$_{13}$NO$_8$P$_2$Ca•H$_2$O (MW 305.18): C, 15.74; H, 4.29; N, 4.59; P, 20.30; Ca, 13.13; Found: C, 15.79; H, 4.14; N, 4.52; P, 20.32; Ca, 13.30.

EXAMPLE 3

Extemporaneous Preparation of Suspensions of Crystalline (ABP)Ca Salt

Micronized crystalline (ABP)Ca was suspended in a suitable vehicle the composition of which was sodium carboxymethylcellulose (10 g/l in deionized distilled water) and sodium chloride (8.8 g/l).

EXAMPLE 4

Preparation of Crystalline (ABP)$_2$Ca Salt

[(4-Amino-1-hydroxybutylidene)-1,1-bisphosphonic acid] monosodium salt trihydrate (3.25 g, 0.01 mmol) was dissolved with heating (at approximately 80° C.) in 100 ml of 0.01M HCl. To this solution was added 5 ml of 1.0M CaCl$_2$ solution with stirring. The crystallization commenced after a 10–30 minute lag period at which time the heating was ceased and the mixture was allowed to cool to room temperature. After the crystallization was complete the crystalline (ABP)$_2$Ca was collected by filtration, washed with a small amount of cold water and air dried for several hours. The yield of crystalline di[(4-amino-1-hydroxybutylidene)-1,1-bisphosphonic acid] monocalcium salt, (ABP)$_2$Ca, was >80%. The stoichiometry of the crystalline salt was confirmed by total elemental analysis and single crystal x-ray analysis.

EXAMPLE 5

Extemporaneous Preparation of Suspensions of Crystalline (ABP)$_2$Ca Salt

Micronized crystalline (ABP)$_2$Ca was suspended in a suitable vehicle the composition of which was sodium carboxymethylcellulose (0.5–1.0% in deionized distilled water), sodium chloride (4.5 g/l) and sodium acetate (6.3 g/l).

EXAMPLE 6

Preparation of Suspensions of Amorphous (ABP)$_3$Ca$_4$ Salt

Step A: Preparation of a Buffered Solution of (4-Amino-1-hydroxybutylidene)-1,1-bisphosphonic acid A mixture of 13.05 g of [(4-amino-1-hydroxybutylidene)-1,1-bisphosphonic acid] monosodium salt trihydrate, 2.60 g of sodium hydroxide, 2.50 g of sodium chloride and 1.10 g of 2-amino-2-hydroxymethyl-1,3-propanediol (Tris) were dissolved in 500 ml of deionized distilled water and the resulting solution was filtered through a 0.22 μm Millipore filter.

Step B: Preparation of a Solution of Calcium Chloride

Calcium chloride dihydrate (8.10 g) was dissolved in 300 ml of deionized distilled water and the resulting solution was filtered through a 0.22 μm Millipore filter.

Step C: Preparation of Suspensions of Amorphous (ABP)$_3$Ca$_4$ Salt

The solution of (4-amino-1-hydroxybutylidene)-1,1-bisphosphonic acid (prepared in Step A) was added to the solution of calcium chloride (prepared in Step B) with vigorous stirring. Amorphous tri[(4-amino-1-hydroxybutylidene)-1,1-bisphosphonic acid] tetracalcium salt, (ABP)$_3$Ca$_4$, precipitated during the mixing to form a finely divided flocculant suspension. The total volume was made up to one liter and the suspension was subdivided and sterilized by autoclave. The stoichiometry of the amorphous salt was determined by back calculation from the known concentrations of starting materials and the supernatant phase following precipitation.

PHARMACOLOGICAL TESTS

Local Irritation Study/Rat Paw Licking Response Test

Group of rats were given the test compound (as a suspension in sodium carboxymethylcellulose, aqueous sodium chloride and aqueous sodium acetate for the (ABP)$_2$Ca, as a suspension in aqueous sodium chloride and Tris buffer for the (ABP)$_3$Ca$_4$ salt and as a solution in isotonic saline buffer for the (ABP)Na salt) at various concentrations by subcutaneous administration in the paw.

As indicated in Table 1, the suspensions of both the (ABP)$_2$Ca salt, or the (ABP)$_3$Ca$_4$ salt induced a lower number of responses and were better tolerated than the solution of the (ABP)Na salt in this test.

TABLE 1

| Treatment | Peak Response* |
|---|---|
| (ABP)$_2$Ca | |
| 5 mg P/ml | 4/12 (2.7) |
| 10 mg P/ml | 5/12 (2.6) |
| 20 mg P/ml | 6/12 (2.7) |
| (ABP)$_3$Ca$_4$ | |
| 5 mg P/ml | 4/12 (3.7) |
| 10 mg P/ml | 3/12 (3.7) |
| 20 mg P/ml | 2/12 (1.5) |
| (ABP)Na | |
| 2.5 mg P/ml | 6/12 (6.3) |

TABLE 1-continued

| Treatment | Peak Response* |
|---|---|
| 1.25 mg P/ml | 2/12 (4.5) |

*Number of rats showing positive response.
Number in parenthesis represent average number of responses per rat.
(Concentrations are expressed as mg ABP per ml)

Effect in Preventing Bone Loss Associated with Immobilization (Study I)

Groups of five male Sprague-Dawley derived rats weighing about 250 grams were given the test compound (as a suspension in sodium carboxymethylcellulose, aqueous sodium chloride and aqueous sodium acetate for the $(ABP)_2Ca$, as a suspension in aqueous sodium chloride and Tris buffer for the $(ABP)_3Ca_4$ salt and as a solution in isotonic saline buffer for the (ABP)Na salt) at a concentration of 1.0 mg P/ml by subcutaneous administration in one dose of either 1.0 mg P/kg or 0.1 mg P/kg each on day -4 before surgery, and in one dose again on day -3 before surgery (dosages are expressed as mg ABP per kg body weight of the subject). It was noted that the suspension of the $(ABP)_2Ca$ salt and the suspension of the $(ABP)_3Ca_4$ salt exhibited a lower tendency to induce irritation at the site of injection relative to the solution of the (ABP)Na salt. On day 0 all rats underwent surgery whereby the sciatic nerve of the right hind limb was severed. Ten days following immobilization surgery, the rats were sacrificed and hind limbs removed. The femora were defleshed, maximum femoral length of both femora measured and then placed in a muffle furnace at 700° C. for 24 hours. Ash weight was then determined and the data are reported in Table 2. As indicated in Table 2, the % bone loss was less for the groups of rats treated with a suspension of either the $(ABP)_2Ca$ salt or the $(ABP)_3Ca_4$ salt, relative to the group of test animals treated with a solution of the (ABP)Na salt.

TABLE 2

| Treatment | mg Diff | se | % Bone Loss | se |
|---|---|---|---|---|
| $(ABP)_2Ca$ (2 × 1.0 mg P/kg) | 7.38 | 3.86 | 2.09 | 1.10 |
| $(ABP)_2Ca$ (2 × 0.1 mg P/kg) | 6.50 | 3.08 | 1.93 | 0.90 |
| $(ABP)_3Ca_4$ (2 × 1.0 mg P/kg) | 3.94 | 2.62 | 1.22 | 0.81 |
| $(ABP)_3Ca_4$ (2 × 0.1 mg P/kg) | 7.68 | 0.98 | 2.48 | 0.37 |
| (ABP)Na (2 × 0.1 mg P/kg) | 14.62 | 2.02 | 4.68 | 0.64 |
| Vehicle (Saline) | 25.62 | 2.05 | 8.32 | 0.63 | n = 5/group
mg Diff = difference in ash weight between the intact femur and the immobilized femur
se = standard error of the mean
% Bone Loss = ash weight difference between the intact femur and the immobilized femur divided by the ash weight of the intact femur

Effect in Preventing Bone Loss Associated with Immobilization (Study II)

Groups of five male Sprague-Dawley derived rats weighing about 250 grams were given the test compound, (as a suspension in sodium carboxymethylcellulose, aqueous sodium chloride and Tris buffer for the (ABP)Ca salt, as a suspension in aqueous sodium chloride and aqueous sodium acetate for the $(ABP)_2Ca$, and as a solution in isotonic saline buffer for the (ABP)Na salt) at a concentration of 1.0 mg P/ml by subcutaneous administration in one dose of 0.1 mg P/kg, 0.01 mg P/kg, 0.001 mg P/kg or 0.0001 mg P/kg each on day -2 before surgery, and in one dose again on day -1 before surgery to produce immobilization (dosages are expressed as mg ABP per kg body weight of the subject). Immobilization was produced by unilateral hind limb sciatic neurectomy. Ten days after surgery the rats were sacrificed, hind limbs removed, and the femora ashed at 700° C. for 24 hours. Ash weight was determined and the difference between the ash weight of the intact limb and immobilized limb calculated and expressed as the mg difference. Per cent difference was calculated as the % difference in ash weight between the intact and immobilized limb. As indicated in Table 3, the % bone loss for the groups of rats treated with a suspension of either the (ABP)Ca salt or the $(ABP)_2Ca$ salt, was comparable to the % bone loss for the group of test animals treated with a solution of the (ABP)Na salt.

TABLE 3

| Compound | Dose (mg P/kg) | mg Diff | se | % Bone Loss |
|---|---|---|---|---|
| (ABP)Ca | 0.0001 | 28.70 | 2.36 | 9.34 |
|  | 0.001 | 25.98 | 2.25 | 7.69 |
|  | 0.01 | 16.72 | 1.54 | 5.01 |
|  | 0.1 | 13.24 | 3.49 | 4.12 |
| $(ABP)_2Ca$ | 0.0001 | 29.64 | 1.51 | 8.93 |
|  | 0.001 | 22.00 | 2.99 | 6.58 |
|  | 0.01 | 12.62 | 2.79 | 3.64 |
|  | 0.1 | 11.32 | 2.06 | 4.14 |
| (ABP)Na | 0.0001 | 31.14 | 2.61 | 9.93 |
|  | 0.001 | 21.32 | 2.44 | 5.95 |
|  | 0.01 | 18.72 | 2.90 | 4.90 |
|  | 0.1 | 14.10 | 3.83 | 4.15 |
| Vehicle (saline) | 0 | 28.40 | 2.48 | 8.68 | n = 5/group
mg Diff = difference in ash weight between the intact femur and the immobilized femur
se = standard error of the mean
% Bone Loss = ash weight difference between the intact femur and the immobilized femur divided by the ash weight of the intact femur While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A pharmaceutical composition comprising an aqueous suspension of from about 0.05% to about 3% ((4-amino-1-hydroxybutylidene)-1,1-bisphosphonic acid) monocalcium salt.

2. The pharmaceutical composition of claim 1 comprising an aqueous suspension of from about 0.1% to about 1% ((4-amino-1-hydroxybutylidene)-1,1-bisphosphonic acid) monocalcium salt.

3. A pharmaceutical composition comprising an aqueous suspension of from about 0.05% to about 3% di((4-amino-1-hydroxybutylidene)-1,1-bisphosphonic acid) monocalcium salt.

4. The pharmaceutical composition of claim 3 comprising an aqueous suspension of from about 0.1% to about 1% di((4-amino-1-hydroxybutylidene)-1,1-bisphosphonic acid) monocalcium salt.

5. A pharmaceutical composition comprising an aqueous suspension of from about 0.05% to about 3% tri((4-amino-1-hydroxybutylidene)-1,1-bisphosphonic acid) tetracalcium salt.

6. The pharmaceutical composition of claim 5 comprising an aqueous suspension of from about 0.1% to about 1% tri ((4-amino-1-hydroxybutylidene)-1,1-bisphosphonic acid) tetracalcium salt.

7. The pharmaceutical composition of claim 1 which additionally comprises sodium carboxymethylcellulose and sodium chloride.

8. The pharmaceutical composition of claim 1 which additionally comprises sodium chloride.

9. The pharmaceutical composition of claim 3 which additionally comprises sodium carboxymethylcellulose and sodium acetate.

10. The pharmaceutical composition of claim 3 which additionally comprises sodium chloride and sodium acetate.

11. The pharmaceutical composition of claim 5 which additionally comprises 2-amino-2-hydroxymethyl-1,3-propanediol and sodium chloride.

12. A method of treating diseases involving bone resorption which comprises the subcutaneous or intramuscular administration to a patient in need of such treatment of the pharmaceutical composition of claim 1.

13. A method of treating diseases involving bone resorption which comprises the subcutaneous or intramuscular administration to a patient in need of such treatment of the pharmaceutical composition of claim 3.

14. A method of treating diseases involving bone resorption which comprises the subcutaneous or intramuscular administration to a patient in need of such treatment of the pharmaceutical composition of claim 5.

15. A method of treating diseases involving bone resorption which comprises the subcutaneous or intramuscular administration to a patient in need of such treatment of the pharmaceutical composition of claim 1 on an intermittent basis.

16. A method of treating diseases involving bone resorption which comprises the subcutaneous or intramuscular administration to a patient in need of such treatment of the pharmaceutical composition of claim 3 on an intermittent basis.

17. A method of treating diseases involving bone resorption which comprises the subcutaneous or intramuscular administration to a patient in need of such treatment of the pharmaceutical composition of claim 5 on an intermittent basis.

18. A method of treating osteoporosis which comprises the subcutaneous or intramuscular administration to the person in need of such treatment of the pharmaceutical composition of claim 1.

19. A method of treating osteoporosis which comprises the subcutaneous or intramuscular administration to the person in need of such treatment of the pharmaceutical composition of claim 3.

20. A method of treating osteoporosis which comprises the subcutaneous or intramuscular administration to the person in need of such treatment of the pharmaceutical composition of claim 5.

* * * * *